United States Patent [19]

Malek et al.

[11] Patent Number: 4,487,253

[45] Date of Patent: Dec. 11, 1984

[54] HEAT EXCHANGER FOR CRYOSURGICAL INSTRUMENTS

[75] Inventors: Zdenek Malek; Stanislav Jelinek; Alexandr Belling; Vladimir Matena; Jan Jelinek, all of Prague, Czechoslovakia

[73] Assignee: Vyzkumny ustav silnoproude elektrotechniky, Prague, Czechoslovakia

[21] Appl. No.: 318,581

[22] Filed: Nov. 5, 1981

[30] Foreign Application Priority Data

Nov. 12, 1980 [CS] Czechoslovakia ............... 7677-80

[51] Int. Cl.³ .................. F28F 1/40; F28D 17/00
[52] U.S. Cl. ...................... 165/11 R; 165/10; 165/179; 62/6; 62/514 R
[58] Field of Search ............ 165/4, 10, 11 R; 62/6, 62/64, 514 R

[56] References Cited

U.S. PATENT DOCUMENTS

| | | | |
|---|---|---|---|
| 3,216,484 | 11/1965 | Gifford | 165/4 |
| 3,692,095 | 9/1972 | Fleming | 165/4 |
| 3,692,099 | 9/1972 | Nesbitt et al. | 165/10 |
| 3,862,546 | 1/1975 | Daniels | 62/6 |
| 4,259,844 | 4/1981 | Sarcia et al. | 62/6 |
| 4,310,337 | 1/1982 | Sarcia | 62/6 |

Primary Examiner—William R. Cline
Assistant Examiner—Edward P. Walker

[57] ABSTRACT

A heat exchanger for cryosurgical instruments comprises a mantle containing individual layers of a heat exchange substance, such as a heat exchange material or a heat exchange filler, an outer jacket surrounding the mantle, a contact zone within the outer jacket for receiving cooling fluid, and a heat detector in thermal contact with the outer jacket but separated by the mantle from the cooling fluid contact zone. Each of the individual layers of heat exchange substance is positioned within the mantle a spaced distance from every other individual layer, so that these individual layers of heat exchange substance are mutually separated from one another.

3 Claims, 4 Drawing Figures

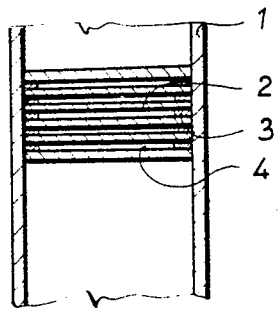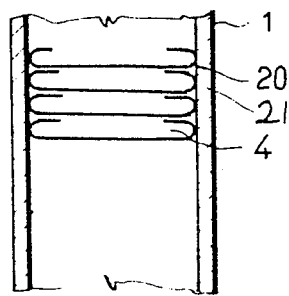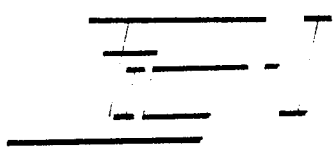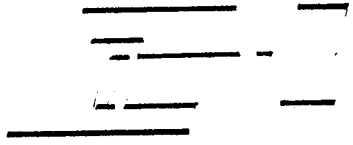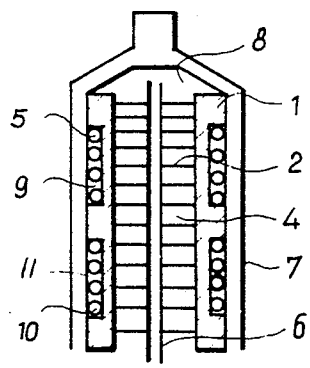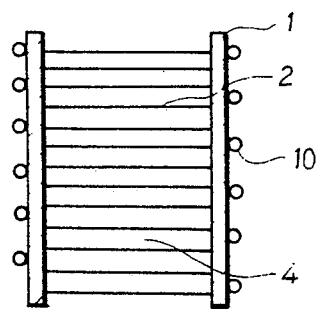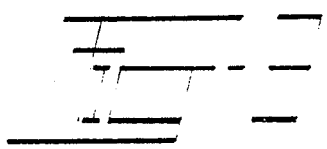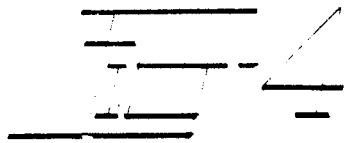

HEAT EXCHANGER FOR CRYOSURGICAL INSTRUMENTS

BACKGROUND OF THE INVENTION

The presently known cryosurgical instruments are usually equipped with two heat exchangers, the first for cooling and the second for heating. The cooling heat exchanger is utilized for heat exchange between a cooling fluid and the operating end piece of the instrument. The heating heat exchanger is utilized for heating the cooling fluid leaving the instrument, whenever the enthalpy of the cooling fluid was not fully used for cooling the tissue adjacent to the operating end piece.

Cooling heat exchangers are known as having the simplest type of chamber construction, whenever the cooling fluid by-passes the cooled-down smooth walls thereof, or by-passes the cooled-down ribbed walls thereof, if these ribbed walls are present in the structure. Cooling heat exchangers may also be of the porous type of chamber construction, being formed usually from metallic grids or from perforated metallic foils, in such a manner that these metallic grids or foils have a good mutual thermal contact with each other.

The heat exchanger will also contain a heat detector and a heating element. The heat detector and the heating element are each so placed within the heat exchanger that each is immersed in the path of, and is washed by, the exit flow of the cooling fluid leaving the heat exchanger. The heating heat exchangers are usually formed by locating heating coils within a stream of the exiting gas leaving the heat exchanger.

The disadvantages of the above-mentioned chamber type of cooling heat exchanger consist of low efficiency caused by the small amount of heat transfer surface area. For example, in order for the chamber type of cooling heat exchanger to be able to achieve a transferring away from the body tissue being operated upon, of an amount of heat measured in units of watts, it becomes necessary for the heat exchanger to consume the cooling fluid at a rate measured in liters per minute.

Cooling heat exchangers equipped with the porous type of components have a higher order of efficiency. However the porous type does have the disadvantages of having its thermal efficiency suppressed due to thermal faults in the direction of flow of the cooling fluid and due to imperfect thermal contact with the outer jacket of the heat exchanger. A similar situation exists as well for the heating type of heat exchangers.

The above-noted disadvantages not only decrease the quality of the cryosurgery performed, but they also substantially increase the quantity of energy needed for utilizing the cryosurgical instrument. Because of the location of the heat detector within the exit flow stream of the cooling fluid leaving the heat exchanger, false information is obtained about the correct temperature at the surface of the cryosurgical instrument. This false information can result in complications during a cryosurgical operation; for example, not attaining the desired low temperature during cryolesis is one disadvantage. Another example of a complication is one which results from the situation wherein the thermometer shows a temperature reading above 0° C., while the correct temperature at the surface of the end of the instrument touching the body tissue, is far below the freezing point. In this situation, there is injury to the tissue caused by the tearing away of tissue frozen together onto the operating end of the cryosurgical instrument.

OBJECTS OF THE INVENTION

It is an object of the present invention to provide a heat exchanger for cryosurgical instruments, in which the heat exchanger contains anisotropic heat exchange material, or heat exchange fillers.

It is another object of the present invention to provide a heat exchanger for cryosurgical instruments, in which the thermal contact between the individual layers of heat exchange material, or fillers, is restricted within the heat exchanger.

It is a further object of the present invention to provide a heat exchanger for cryosurgical instruments, in which the thermal conductivity of the heat exchanger is suppressed in the direction of flow of the cooling fluid through the heat exchanger, while maintaining the thermal conductivity in a direction perpendicular to the flow of the cooling fluid through the heat exchanger.

It is another object of the present invention to provide a heat exchanger for cryosurgical instruments, in which the heat exchanger contains a heat detector which is separated from the space through which the cooling fluid flows through the heat exchanger.

These and further objects of the present invention will become more apparent as the description thereof proceeds.

THE DRAWINGS

The present invention will also be described by reference to the following drawings which are not to be deemed limitative of the invention in any manner thereof.

FIG. 1 shows a longitudinal section view of a portion of a heat exchanger, either for cooling or for heating, having individual layers of heat exchange material with separating elements inserted between these layers.

FIG. 2 shows a longitudinal section view of a portion of a heat exchanger, either for cooling or for heating, having individual layers of heat exchange fillers so shaped as to restrict the thermal contact between these layers.

FIG. 3 shows a longitudinal section view of the construction of a cooling heat exchanger capable of measuring the correct temperature at the surface of the cooling exchanger.

FIG. 4 shows a longitudinal section view of the construction of the heating section of a heating heat exchanger.

DESCRIPTION OF THE INVENTION

The present invention relates to a heat exchanger for cryosurgical instruments, in which the heat exchanger contains an anisotropic heat exchange substance, such as an anisotropic heat exchange material or an anisotropic heat exchange filler.

The disadvantages of the prior art devices are substantially eliminated by using the heat exchanger of the present invention, which comprises having in the mantle, or inner jacket, of the heat exchanger, individual layers of a heat exchange substance selected from the group comprising a heat exchange material or a heat exchange filler, and between these layers are located gaps, or spaced distances, such that these individual layers of heat exchange substance are mutually separated.

There are two embodiments according to the present invention.

In the first embodiment, the heat exchange substance is a porous heat exchange material; and separating elements are placed between the individual layers of porous heat exchange material in the mantle. The porous heat exchange material is preferably made from metallic grids having high thermal conductivity composed, for example, of a copper alloy or of an aluminum alloy. Perforated metallic foils could also be used as the porous heat exchange material. The separating elements are made from a thermal insulator, for example, heat and cold resistant glass or heat and cold resistant ceramic or heat and cold resistant plastic material. These separating elements between the layers create gaps, or spaced distances, between the layers such that the individual layers of heat exchange material are mutually separated. In this embodiment the metallic grids are preferably disc shaped.

In the second embodiment which is preferred, the heat exchange substance is a porous heat exchange filler. In this second embodiment, it is possible to use the same porous heat exchange filler throughout the mantle, instead of having to use separating elements between the individual layers of porous heat exchange material, as in the first embodiment. The porous heat exchange fillers are preferably made from metallic grids having high thermal conductivity composed, for example, of a copper alloy or of an aluminum alloy. Perforated metallic foils could also be used as the porous heat exchange filler. Each individual layer of heat exchange filler is so shaped as to restrict the thermal contact between these layers. These heat exchange fillers are so shaped as to create gaps, or spaced distances, between the layers of heat exchange filler, such that the individual layers of heat exchange filler are mutually separated. In this embodiment the metallic grids are preferably circular in shape and have a peripheral outer border resembling a lip which has been folded over and back upon itself.

In both embodiments the term metallic grid refers to a structure similar to a wire mesh in which the individual metal strands are joined together in a regular pattern with spaces created between the points of intersection and connection of the metal strands.

The term cooling fluid refers to an inert low temperature liquid or gas, such as liquid nitrogen, which is capable of cooling the cryosurgical instrument down to a temperature low enough to enable this device to achieve its intended results.

The above-mentioned disadvantage, wherein there is an inaccurate measurement of the surface temperature of the cryosurgical instrument of the prior art, is eliminated by means of another aspect of the present invention. This improved result is based upon locating the heat detector outside of the space through which the cooling fluid flows, and shielding the heat detector from direct contact with the cooling fluid.

The term heat detector refers to a temperature sensitive device, such as a thermistor or a thermocouple, which can be used to correctly measure the temperature at the outer surface of the cryosurgical instrument.

There is a substantial improvement in the anisotropic properties of the heat exchanger, which is achieved by restricting the thermal contact between the individual layers of heat exchange material, or fillers, within the exchanger. This restriction of thermal contact causes a suppression of thermal conductivity in the direction of flow of the cooling fluid and thus causes an increase in the thermal gradient inside the heat exchange material, or fillers, in this same flow direction. The result is the achieving of an increase in the efficiency of heat transfer from the outside surface of the heat exchanger into the cooling fluid. Therefore it is possible to reduce the amount of cooling fluid passed through the cooling type of heat exchanger, and to decrease the quantity of electricity consumed in the heating type of heat exchanger, while maintaining the same thermal capacity.

Referring now to the drawings, FIG. 1 shows a longitudinal section view of a portion of a heat exchanger, either for cooling or for heating. The mantle, or inner jacket, 1 of the heat exchanger contains individual layers of porous heat exchange material 2 having a high thermal conductivity, with thermally insulating separating elements 3 interposed between these layers. Due to this interposition of the separating elements 3, each of the individual layers 2 is positioned within the mantle 1 a spaced distance, creating a gap, 4 from every other individual layer, so that the individual layers of heat exchange material are mutually separated from one another. This mutual separation of the individual layers acts so as to restrict the thermal contact between these layers.

FIG. 2 shows a longitudinal section view of a portion of a heat exchanger, either for cooling or for heating. In this embodiment, which is preferred, the mantle, or inner jacket, 1 of the heat exchanger is devoid of the separating elements 3 of FIG. 1. Instead, the heat exchange material 2 of FIG. 1 is replaced in FIG. 2 by individual layers of porous heat exchange fillers 20 which are so shaped as to restrict the thermal contact between these individual layers. In this embodiment the porous heat exchange fillers are metallic grids which are circular in shape and have a peripheral outer border resembling a lip 21 which has been folded over and back upon itself. Due to this specific shaping of the heat exchange fillers 20, each of the individual layers is positioned within the mantle 1 a spaced distance, creating a gap, 4 from every other individual layer, so that the individual layers of heat exchange fillers are mutually separated from one another.

The mantle 1 is composed of a metal having a high thermal conductivity. The heat exchange material 2, or the heat exchange filler 20, is joined to the mantle in such a manner as to insure a high rate of heat transfer across the interface at this interconnection. Such methods of joining include sintering, brazing, soldering or by very tight mechanical contact. As a specific example of a joining technique, vacuum diffusion soldering may be utilized for permanently connecting the heat exchange material 2, or the fillers 20, to the mantle 1.

FIG. 3 shows a longitudinal section view of the construction of a cooling heat exchanger capable of measuring the correct temperature at the surface of the cooling exchanger. The heat exchanger has an outer jacket, or bush, 7 surrounding the mantle, or inner jacket, 1 and the individual layers of heat exchange material 2 or the individual layers of heat exchange fillers 20 (not shown). Within the outer jacket 7 are means defining a contact zone 8 for receiving the cooling fluid of the heat exchanger. An inlet fluid flow tube 6 extends into the heat exchanger and extends through the individual layers of heat exchange material 2, or heat exchange fillers 20 (not shown); and tube 6 is terminated in the contact zone 8 of the outer jacket 7. The inlet fluid flow tube 6 has a longitudinal axis parallel to the longitudinal axis of the mantle 1.

The mantle 1 further comprises a first heat exchange chamber 9 containing a heat detector 5. The heat exchange chamber 9 and the heat detector 5 are both separated by the mantle 1 from the means defining the contact zone 8 which receives the cooling fluid for the heat exchanger. The heat detector 5 is in thermal contact with the outer jacket 7.

Mantle 1 also contains heating element 10 located in a second heat exchange chamber 11.

FIG. 4 shows a longitudinal section view of the construction of the heating section of a heating heat exchanger. Mantle 1 contains individual layers of porous heat exchange material 2, or fillers 20 (not shown), having a high thermal conductivity. Each of the individual layers is positioned within the mantle 1 a spaced distance, creating a gap, 4 from every other individual layer, so that the individual layers of heat exchange material are mutually separated from one another. This mutual separation of the individual layers acts so as to restrict the thermal contact between these layers. Surrounding the walls of mantle 1 and being in good thermal contact with the walls of the mantle is the heating element 10. Examples of the heating element 10 include a coil of high resistance heating wire, or an induction heating coil.

The present invention will be further described by reference to the following examples which are not to be deemed limitative of the invention in any manner thereof.

EXAMPLE 1

The heat exchanger of FIG. 3 can be utilized as a cooling heat exchanger in the following manner. A cooling fluid, such as liquid nitrogen at a temperature at or below its boiling point of $-195.8°$ C., is introduced into the heat exchanger and is conducted through the inlet fluid flow tube 6. The liquid nitrogen flows through tube 6 into contact zone 8 which receives this cooling fluid. In zone 8 it impinges upon outer jacket 7 and directly cools the outer jacket at this stage of the cooling process.

Means defining the contact zone 8 deflect the impinging cooling fluid, usually in a backward direction, away from the outer jacket 7 and onto the mantle 1, as well as onto the heat exchange material 2, or onto the heat exchange fillers 20 (not shown). When this deflected cooling fluid makes contact with the heat exchange material 2, or with fillers 20 (not shown), the porous metallic grids thereof conduct heat directly away from the mantle 1 and indirectly away from the outer jacket 7 by means of heat transfer through the mantle. This heat is absorbed by the cooling fluid liquid which might soon thereafter begin to boil, so that the liquid and gaseous phases might then be present together. The deflected cooling fluid may also make contact directly with the mantle 1 and conduct heat directly away from the mantle 1 and indirectly away from the outer jacket 7, by means of the good thermal contact between the mantle and the outer jacket.

The temperature of the outer jacket 7 is correctly measured by the heat detector 5 in the first heat exchange chamber 9. Heating element 10 in the second heat exchange chamber 11 is capable of heating the outer jacket 7 whenever necessary. For example, after a cryosurgical operation has been completed, and the flow of cooling fluid has been terminated, then the cryosurgical instrument can be heated back up to room temperature.

EXAMPLE 2

The heat exchanger of FIG. 4 can be utilized as a heating heat exchanger in the following manner. A gaseous nitrogen leaving the cooling exchanger is introduced into the heating heat exchanger. As this relatively cold gaseous nitrogen flows through the heat exchange material 2, heat from the heating element 10 is transferred through the mantle 1 and then through the heat exchange material 2, or the heat exchange fillers 20 (not shown), and is further transferred into the gaseous nitrogen so as to heat up this gas before it leaves the cryosurgical instrument.

The present invention has the following advantages. There is an increased rate of heat transfer from the mantle of the heat exchanger into the cooling fluid. This increases the cooling rate at the surface of the cryosurgical instrument, and thus produces a sharper localization of cryolesis in the tissue being operated upon. There is a substantial reduction in the quantity of cooling fluid consumed in order to absorb a given amount of heat energy during the utilization of the cryosurgical instrument. Thus it is possible to substantially decrease the weight of this instrument, as well as improving its controllability. Also the present invention overcomes the disadvantages of known prior art heat exchangers, in that it suppresses the thermal conductivity of the heat exchanger in the direction of flow of the cooling fluid through the heat exchanger, while maintaining the thermal conductivity in a direction perpendicular to the flow of the cooling fluid, through the heat exchanger. These desired results produced by the invention are achieved by restricting the thermal contact between the individual layers of heat exchange material, or fillers, within the heat exchanger. A further advantage is that the proper functioning is assured for the heat detector placed within the cooling type of heat exchanger. This result is achieved by separating and shielding the heat detector from the space through which the cooling fluid flows through the heat exchanger.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

What is claimed is:

1. A heat exchanger for cryosurgical instruments comprising a mantle containing individual layers of a heat exchange substance selected from the group consisting of a heat exchange material and a heat exchange filler, an outer jacket surrounding said mantle and said individual layers of heat exchange substance, means defining a contact zone within said outer jacket for receiving the cooling fluid of said heat exchanger, said mantle further comprising a first heat exchange chamber containing a heat detector, said heat exchange chamber and said heat detector both being separated by said mantle from said means defining said contact zone, and wherein said heat detector is in thermal contact with said outer jacket, and each of said individual layers is positioned within said mantle a spaced distance from every other individual layer, so that said individual layers of said substance are mutually separated from one another.

2. The heat exchanger of claim 1, further comprising an inlet fluid flow tube which extends into the heat exchanger and through said individual layers of heat exchange substance and is terminated in said contact zone of said outer jacket, and said inlet fluid flow tube having a longitudinal axis parallel to the longitudinal axis of said mantle.

3. The heat exchanger of claim 1, wherein said mantle further comprises a second heat exchange chamber containing a heating element.

* * * * *